United States Patent [19]

Spellmeyer et al.

[11] Patent Number: 5,447,916
[45] Date of Patent: Sep. 5, 1995

[54] PEPTOID ALPHA-1 ADRENERGIC RECEPTOR LIGANDS

[75] Inventors: David C. Spellmeyer, Alameda; Walter H. Moos, Oakland; Eric J. Martin, El Cerrito; Ronald N. Zuckermann, Berkeley; Gregory Stauber, Danville, all of Calif.

[73] Assignee: Chiron Corporation, Emeryville, Calif.

[21] Appl. No.: 99,908

[22] Filed: Jul. 30, 1993

[51] Int. Cl.$^6$ .................. C07K 5/023; C07K 5/083; A61K 38/05; A61K 38/06
[52] U.S. Cl. .................. 514/18; 260/998.2; 514/19; 514/464; 514/465; 514/466; 514/615; 514/616; 514/821; 514/824; 514/913; 530/331; 549/438; 549/439; 549/441; 564/149; 564/150; 564/153; 564/157
[58] Field of Search ............... 260/998.2; 514/18, 19, 514/464, 465, 466, 615, 616, 821, 824, 913; 530/331; 549/438, 439, 441; 564/149, 150, 153, 157, 158

[56] References Cited

U.S. PATENT DOCUMENTS 4,254,106  3/1981  Wilkinson ............... 424/177

*Primary Examiner*—Peter O'Sullivan
*Attorney, Agent, or Firm*—Grant D. Green; Robert P. Blackburn

[57] ABSTRACT

Compounds of the formula:

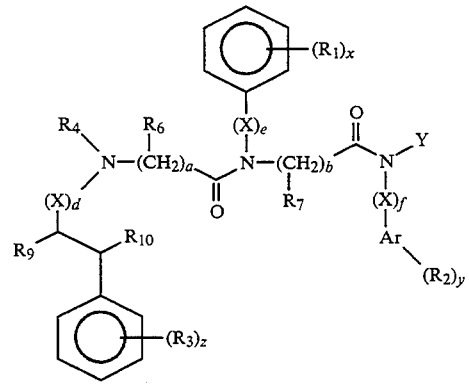

are useful for treating conditions modulated by $\alpha_1$-adrenergic receptors.

13 Claims, No Drawings

PEPTOID ALPHA-1 ADRENERGIC RECEPTOR LIGANDS

DESCRIPTION

1. Technical Field

This invention relates generally to the fields of biochemistry and medicinal chemistry. More specifically, the invention relates to peptoids which bind to α1-adrenergic receptors.

1. Background of the Invention

Alpha-adrenergic receptors are divided into two subtypes ($\alpha_1$ and $\alpha_2$) based on their drug selectivity. Alpha$_1$-adrenergic receptors ($\alpha_1$AR) are found primarily post-synapse on target cells. Activation of $\alpha_1$AR provokes an increase in intracellular free $Ca^{2+}$ concentration. In blood vessels and smooth muscle, this causes contraction of the tissue. Stimulation of $\alpha_1$AR in heart tissue results in positive inotropic effects: general stimulation results in the CNS. Other $\alpha_1$AR are found in the eye and liver.

Most $\alpha_1$AR ligands are therapeutically useful as antihypertensive agents. However, $\alpha_1$AR antagonists have also been found useful in the treatment of benign prostatic hyperplasia (see, e.g., K. Maruyama et al., *J Pharmacobio-Dyn* (1991)14:315–19).

DISCLOSURE OF THE INVENTION

One aspect of the invention is a compound of Formula 1:

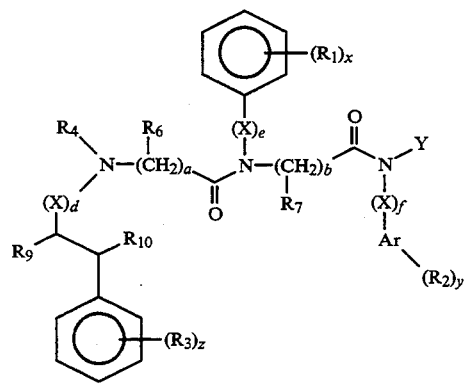

wherein

Ar is phenyl, benzyl, phenethyl, naphthyl, 3,4-methylenedioxyphenyl, or

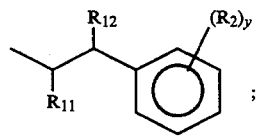

X is —NH— or —$CH_2$—;

Y is H, lower alkyl, aryl, aryl-lower alkyl, acyl or

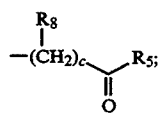

each $R_1$, $R_2$, and $R_3$ is independently H, OH, $NH_2$, $NO_2$, halo, lower alkyl, halo-lower alkyl, lower alkoxy, halo-lower alkoxy, lower alkoxy-lower alkyl, hydroxy-lower alkyl, hydroxy-lower alkoxy, lower alkoxy-carbonyl, aryl, aryloxy, aryl-lower alkyl, aryloxy-lower alkyl, or

where $R_{13}$ is H, OH, $NH_2$, halo, lower alkyl, halo-lower alkyl, lower alkoxy, halo-lower alkoxy, lower alkoxy-carbonyl, aryl, aryloxy, aryl-lower alkyl, or aryloxy-lower alkyl;

$R_4$ is H, lower alkyl, aryl, aryl-lower alkyl, or acyl;

$R_5$ is OH, $NH_2$, OR, or NHR, where R is lower alkyl, aryl, or aryl-lower alkyl;

$R_6$, $R_7$, and $R_8$ are each independently H, lower alkyl, aryl, or aryl-lower alkyl;

$R_9$ and $R_{11}$, are each independently H, lower alkyl, aryl, or aryl-lower alkyl;

$R_{10}$ and $R_{12}$ are each independently H, lower alkyl, aryl, aryl-lower alkyl, halo, or hydroxy;

a, b, and c are each independently 1 or 2;

d, e, and f are each independently 0 or 1;

w, x, y, and z are each independently 0, 1, 2, 3, 4, or 5;

and pharmaceutically acceptable salts, esters, and amides thereof.

Another aspect of the invention is a method for identifying $\alpha_1$-adrenergic receptors, by contacting $\alpha_1$-adrenergic receptors with a compound of formula 1 and detecting binding.

Another aspect of the invention is a method for treating a subject having a condition susceptible to treatment with an $\alpha_1$-adrenergic receptor agonist or antagonist, comprising administering to said subject an effective amount of a compound of Formula 1.

Another aspect of the invention is a composition for treating a subject having a condition susceptible to treatment with an $\alpha_1$-adrenergic receptor agonist or antagonist, comprising an effective amount of a compound of Formula 1 in combination with a pharmaceutically acceptable excipient.

Another aspect of the invention is a method for identifying the presence of $\alpha_1$-adrenergic receptors in a preparation, comprising contacting said preparation with a compound of Formula 1, and detecting binding of said compound to said preparation.

MODES OF CARRYING OUT THE INVENTION

A. Definitions

"Compound of Formula 1" refers to a compound of the formula

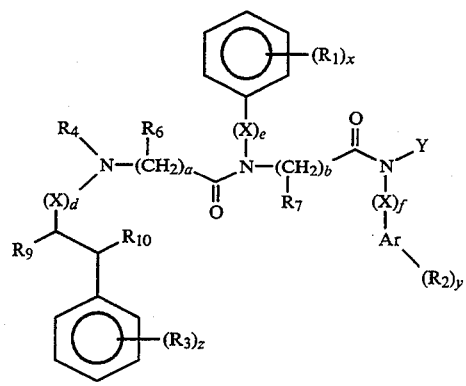

wherein

Ar is phenyl, benzyl, phenethyl, naphthyl, 3,4-methylenedioxyphenyl, or

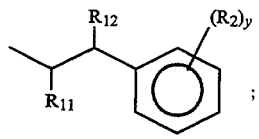

X is —NH— or -CH$_2$—;

Y is H, lower alkyl, aryl, aryl-lower alkyl, acyl or

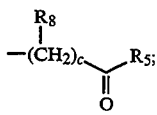

each $R_1$, $R_2$, and $R_3$ is independently H, OH, NH$_2$, NO$_2$, halo, lower alkyl, halo-lower alkyl, lower alkoxy, halo-lower alkoxy, lower alkoxy-lower alkyl, hydroxy-lower alkyl, hydroxy-lower alkoxy, lower alkoxy-carbonyl, aryl, aryloxy, aryl-lower alkyl, aryloxy-lower alkyl, or

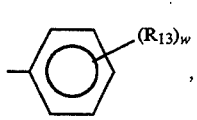

where $R_{13}$ is H, OH, NH$_2$, halo, lower alkyl, halo-lower alkyl, lower alkoxy, halo-lower alkoxy, lower alkoxy-carbonyl, aryl, aryloxy, aryl-lower alkyl, or aryloxy-lower alkyl;

$R_4$ is H, lower alkyl, aryl, aryl-lower alkyl, or acyl;

$R_5$ is OH, NH$_2$, OR, or NHR, where R is lower alkyl, aryl, or aryl-lower alkyl:

$R_6$, $R_7$, and $R_8$ are each independently H, lower alkyl, aryl, or aryl-lower alkyl;

$R_9$ and $R_{11}$, are each independently H, lower alkyl, aryl, or aryl-lower alkyl;

$R_{10}$ and $R_{12}$ are each independently H, lower alkyl, aryl, aryl-lower alkyl, halo, or hydroxy;

a, b, and c are each independently 1 or 2;

d, e, and f are each independently 0 or 1;

w, x, y, and z are each independently 0, 1, 2, 3, 4, or 5;

and pharmaceutically acceptable salts, esters, and amides thereof.

The term "peptoid" refers to monomers other than the twenty conventional amino acids and the common nucleotides and nucleosides (i.e., the DNA bases dA, dC, dG, and dT, and the RNA bases A, C, G, and U). The terms "amide peptoid" and nonconventional amino acid" refer to peptoids which are linked together through amide (peptide) bonds. Amide polypeptoid bonds may include substituents on the amide nitrogen atom. Presently preferred peptoids include those wherein the sidle chain (the residue attached to the backbone N) is selected from the following: 2-hydroxyethyl, 3-hydroxypropyl, 2-(4-hydroxyphenyl)ethyl, 2-(phenyl)ethyl, 2,2-diphenylethyl, 1-naphthylmethyl, 4-(phenyl)phenyl, methyl, 2-methylpropyl, 2-methoxyethyl, pentyl, 1-ethylpropyl, cyclohexyl, (1-tetrahydrofuryl)methyl, 4-(phenoxy)phenyl, 3,4-methylenedioxybenzyl, 3,4-dimethoxybenzyl, 2-aminoethyl, 2-(N-morpholino)ethyl, 2-carboxyethyl, 2-(2-(2-aminoethoxy)ethoxy)ethyl, 2-methoxypyrid-5-yl, adamantyl, 1-hydroxy-1-phenylprop-2-yl, 4-ethenylphenyl, 4-biphenyl, 3-biphenyl, 4-butylphenyl, 4-cyclohexylphenyl, 4-iodophenyl, 2,2-diphenylethyl, 4-trifluoromethylbenzyl, 2-(4-chlorophenyl)ethyl, 2-(cyclohex-1-enyl)ethyl, 2-phenoxyethyl, 2-phenethylamino, 2-(4-sulfonamidophenyl)ethyl, 3,4-dihydroxyphenethyl, 4-nitrophenethyl, 2-(4-hydroxyphenyl)-2-hydroxyethyl, 2-(4-aminophenyl)ethyl, and 6,7-dimethoxytetrahydroisoquinolinyl.

N-substituted glycine monomers are named Nxxx, where xxx is the multi-letter abbreviation for the amino acid that has the corresponding side chain. An "h" immediately following the N indicates that the monomer is a homolog, having an additional —CH$_2$— between the nitrogen atom and the rest of the side chain (e.g., Nhhis has imidazolylethyl rather than imidazolylmethyl as its side chain). An "m" following the N indicates an α-methyl residue (i.e., an N-substituted alanine instead of an N-substituted glycine): a "p" indicates an α-phenyl residue. A "p" following the N indicates that the backbone is β-alanine (3-aminopropanoic acid) rather than glycine. A "" following the N indicates that that the submonomer used is a hydrazine derivative, resulting in an N—N bond between the side chain and the backbone:

| | |
|---|---|
| Nala = N-methylglycine (sarcosine); | Nasp = N-(carboxy-methyl)glycine; |
| Nglu = N-(2-carboxyethyl)glycine; | Nphe = N-benzylglycine; |
| Nhhis = N-(imidazolylethyl)glycine; | Nile = N-(1-methylpropyl)glycine; |
| Nlys = N-(4-aminobutyl)glycine; | Nleu = N-(2-methylpropyl)glycine; |
| Nmet = N-(2-methylthioethyl)glycine; | Nhser = N-(hydroxyethyl)glycine; |
| Nasn = N-(carbamylmethyl)glycine; | Ngln = N-(2-carbamylethyl)glycine; |
| Nval = N-(1-methylethyl)glycine; | . Narg = N-(3-guanidinopropyl)glycine; |
| Nhtrp = N-(3-indolylethyl)glycine; | Nhtyr = N-(p-hydroxyphenethyl)glycine; |
| Nthr = N-(1-hydroxyethyl)glycine; | Ncys = N-(thiomethyl)glycine |
| Norn = N-(3-aminopropyl)glycine; | Nhphe = N-(2-phenethyl)glycine; |
| Ncpro = N-cyclopropylglycine; | Ncbut = N-cyclobutyglycine; |
| Nchex = N-cyclohexylglycine; | Nchep = N-cycloheptylglycine; |

| | |
|---|---|
| Ncoct = N-cyclooctylglycine; | Ncdec = N-cyclodecylglycine; |
| Ncund = N-cycloundecylglycine; | Ncdod = N-cyclododecylglycine; |
| Nbhm = N-(2,2-diphenylethyl)glycine; | Nbhe = N-(3,3-diphenylpropyl)glycine; |
| Nbiph = N-(4-phenyl)phenylglycine; | Npop = N-(4-phenoxyphenyl)glycine; |
| Nmhphe = N-(2-phenethyl)alanine; | Nphphe = N-(2-phenethyl)beta-alanine; |
| Nphtyr = N-(p-hydroxyphenethyl)beta-alanine; | |
| Npbiph = N-(4-phenyl)phenylbeta-alanine; | |
| Nnbhm = N-(N-(2,2-diphenylethyl)carbamylmethyl)glycine; | |
| Nnbhe = N-(N-(3,3-diphenylpropyl)carbamylmethyl)glycine; | |
| Nbmc = 1-carboxy-1-(2,2-diphenylethylamino)cyclopropane; | |
| Naeg = N-(2-aminoethyl)glycine; | |
| Nzhphe = N-(2-phenethylamino)glycine [or 2-phenethylhydrazopropanoic acid]; | |
| Nzhtyr = N-(p-hydroxyphenethylamino)glycine; and | |
| Noco = N-(3,4-methylenedioxyphenethyl)glycine. | |

The term "lower alkyl" as used herein refers to straight, branched, and cyclic chain hydrocarbon radicals having from 1 to 8 carbon atoms, such as methyl, ethyl, propyl, isopropyl, n-butyl, s-butyl, t-butyl, n-pentyl, n-hexyl, cyclopentyl, cyclohexyl, 2-methylcyclopentyl, cyclopentylacetyl, and the like. "Lower alkoxy" refers to radicals of the formula —OR, where R is lower alkyl as defined above. "Hydroxy-lower alkyl" refers to radicals of the formula HO—R—, where R is lower alkylene of 1 to 8 carbons, and may be straight, branched, or cyclic. "Hydroxy-lower alkoxy" refers to radicals of the formula HO—R—O—, where R is lower alkylene of 1 to 8 carbons, and may be straight, branched, or cyclic. "Lower alkoxy-lower alkyl" refers to groups of the formula $R_aO-R_b-$, where $R_a$ and $R_b$ are each independently lower alkyl. "Lower alkoxy-lower alkoxy" refers to groups of the formula $R_aO-R_bO-$, where $R_a$ and $R_b$ are each independently lower alkyl. "Aryl" refers to aromatic hydrocarbons having up to 14 carbon atoms, preferably phenyl or naphthyl. "Aryl-lower alkyl" refers to radicals of the form Ar—R—, where Ar is aryl and R is lower alkyl. "Aryloxy" refers to radicals of the form Ar—O—, where Ar is aryl. "Aryloxy-lower alkyl" refers to radicals of the form ArO—R—, where Ar is aryl and R is lower alkyl.

The term "acyl" refers to a radical of the formula RCO—, in which R is H, lower alkyl as defined above, phenyl, benzyl or naphthyl. Exemplary acyl groups include acetyl, propionyl, formyl, t-butoxycarbonyl, benzoyl, and the like.

The term "halo" refers to a halogen radical, such as F, Cl, Br, or I.

The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment of a cancer patient may be reduction of tumor size, elimination of malignant cells, prevention of metastasis, or the prevention of relapse in a patient who has been cured. Treatment of infection includes destruction of the infecting agent, inhibition of or interference with its growth or maturation, neutralization of its pathological effects, and the like. Treatment of hypertension includes reducing systolic and/or diastolic blood pressure, in addition to arresting increasing blood pressure or reducing the rate of blood pressure increase due to other causes.

The phrase "condition susceptible to treatment with an $\alpha_1$-adrenergic receptor agonist or antagonist" refers to pathological conditions such as hypertension and benign prostatic hyperplasia which may be treated with an $\alpha_1$AR agonist or an $\alpha_1$AR antagonist. Exemplary conditions include, without limitation, hypertension, benign prostatic hyperplasia, arrhythmia, myocardial ischemia, elevated serum lipid concentrations, glaucoma, and the like (see, e.g., P.B.M.W.M. Timmermans et al., "Comprehensive Medicinal Chemistry, Vol. 3" (Chapter 12.1, pp. 133–85) (Ed. C. Hansch, Pergamon Press); J. E. Humphreys et al., *J Clin Pharm Therapeutics* (1989) 14:263–83). Conditions susceptible to treatment with an $\alpha_1$-adrenergic receptor agonist or antagonist may be determined using simple in vitro or in vivo assays known in the art (see e.g., T. Baum et al., *Am J Med* (1983) 75(4A):15–23; V. A. Alabaster, et al., *Brit J Clin Pharmacol* (1986) 21(Suppl 1):9S-17S; and H. Suzuki et al., *Gen Pharmacol* (1987) 18:171–77).

The term "preparation" refers to a sample to he tested for the presence of $\alpha_1$AR. Preparations may be whole tissues, tissue homogenates, host cells (e.g., recombinant host cells), biopsy samples, blood and/or blood fractions, lymph, and the like.

B. General Method

Compounds of the invention are easily synthesized by standard chemical methods. The presently-preferred method of synthesis is the "submonomer" technique described by R. Zuckermann et al., *J Am Chem Soc* (1992) 114:10646–7, incorporated herein by reference. Briefly, an activated solid-phase synthesis resin is treated to remove any protecting or capping groups, then acylated with an acetic acid derivative having a good leaving group (e.g., bromoacetic acid) under standard conditions. The leaving group is then displaced in an $S_N2$ displacement reaction using an amine corresponding to the desired side chain, producing a secondary amine. The resulting secondary amine is then acylated with an acetic acid derivative, and the cycle repeated for each desired sidechain. Compounds in which $R_6$, $R_7$ and/or $R_8$ are residues other than H are synthesized by employing an acetic acid derivative incorporating the desired residue. Thus, where $R_8$ is methyl one would employ 2-bromopropanoic acid.

For example, to synthesize the compound Nhtyr-Nbiph-Nhphe, the acylated resin is treated with phenethylamine (to provide the homo-Phe side chain), acylated with bromoacetic acid, the bromine displaced with 4-aminobiphenyl (to provide the 4-(phenyl)phenyl side chain), acylated with bromoacetic acid, and the bromine displaced with 4-hydroxyphenethylamine (to provide the homo-Tyr side chain). The last amine may be further acylated or alkylated to reduce the basicity of the compound. The compound is then cleaved from the resin using standard methods, providing either an acid or an amide, depending upon the cleavage conditions. In either case, the terminal carbonyl function may be converted to an amide, acid, aldehyde, alcohol, amine or other group as desired. The final compound is typically purified by chromatography. If desired, simple acid addition salts and/or esters may be prepared using standard techniques.

Compounds of the invention may also be prepared by traditional solution-phase synthesis, beginning with an ester of bromoacetic acid, and proceeding as described above. Alternatively, one may synthesize compounds in the N→C direction in the solution phase, using complete monomers (rather than "submonomers"). For example, Fmoc-protected Nhtyr (with Fmoc protecting the amine) may be condensed with Nbiph-tBu ester with N,N-diisopropylcarbodiimide (DIC) in $DIEA/CH_2Cl_2$ to form (Fmoc)Nhtyr-Nbiph-tBu. The tBu ester is then removed with trifluoroacetic acid (TFA) and scavengers, and the compound condensed with Nhphe-tBu ester to form (Fmoc)Nhtyr-Nbiph-Nhphe-tBu. The compound is then deprotected using TFA, scavengers, and pyrrolidine to provide Nhtyr-Nbiph-Nhphe. Alternatively, one may use tBOC-protected Nhtyr, and employ methyl. esters of Nbiph and Nhphe, cleaving the esters with NaOH rather than TFA with scavengers. It may be necessary to isolate intermediate stage compounds, e.g., by chromatography or fractional crystallization.

The reactants employed in synthesis of the compounds are generally commercially available. Other reactants (e.g., less-common substituted amines) may be prepared by standard chemical means from amines that are commercially available.

Compounds of the invention may be assayed for activity using standard protocols. For example, one may employ the protocol demonstrated in the Examples below to determine binding of compounds of the invention to any desired receptor subtype (e.g., using different sources of tissue). Compounds which exhibit strong binding to receptors will exert either agonistic or (more usually) antagonistic activity, which may be determined by means of appropriate tissue-based or in vivo assays known in the art.

The compounds of the invention may be administered by a variety of methods, such as intravenously, orally, intramuscularly, intraperitoneally, bronchially, intranasally, and so forth. The preferred route of administration will depend upon the nature of the compound and the condition to be treated. Compounds may be administered orally if well absorbed and not substantially degraded upon ingestion (compounds of the invention are generally resistant to proteases). The compounds may be administered as pharmaceutical compositions in combination with a pharmaceutically acceptable excipient. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, sustained-release patches, and the like. Alternatively, one may incorporate or encapsulate the compound in a suitable polymer matrix or membrane, thus providing a sustained-release delivery device suitable for implantation near the site to be treated locally. Other devices include indwelling catheters and devices such as the Alzet® minipump. Further, one may provide the compound in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

Compounds of the invention may be used to detect the presence of $\alpha_1AR$ in tissues, cells, body fluids, and the like, exploiting the fact that compounds of the invention bind to $\alpha_1AR$. In general, a sample is obtained, and is contacted with a compound of the invention under physiological conditions. The sample is then rinsed, and examined for binding of the compound. Examination may be facilitated by using labeled compound (e.g., radiolabeled with $^3H$, $^{13}C$, $^{125}I$, and the like). This assay may be useful, inter alia, for examining expression of $\alpha_1AR$ in recombinant host cells, and for studying pathological distributions of $\alpha_1AR$.

EXAMPLES

The examples presented below are provided as a further guide to the practitioner of ordinary skill in the art, and are not to be construed as limiting the invention in any way.

Example 1

Synthesis of Compounds

A.) General Synthesis of Compounds

Oligomer synthesis was performed on a Rink amide polystyrene resin (0.61 mmol/g, 1% crosslinked, 100–200 mesh). N,N-Dimethylformamide (DMF), dimethylsulfoxide (DMSO), methylene chloride, glacial acetic acid and trifluoroacetic acid (TFA) were obtained from commercial suppliers and used without further purification. Piperidine, bromoacetic acid, N,N-diisopropylcarbodiimide (DIC), phenethylamine, 4-aminobiphenyl, tyramine, and other reagents were obtained from Aldrich and used without further purification.

All reactions were performed at room temperature in a 2.0 L vessel equipped with a 10 cm coarse glass frit. Agitation of the resin-reagent slurry was performed at every step by rotary shaking at 200 rpm. Filtration of the resin-reagent slurry was achieved by the application of vacuum.

A 2.0 L vessel was charged with Rink amide resin (10(3 g, 0.061 mol). The resin was briefly swelled in DMF (1.5 L) with gentle agitation and drained. The 9-fluorenylmethoxycarbonyl (Fmoc) group was then removed by treatment with 20% piperidine/DMF (1.7 L, 1×5 min, followed by 1×20 min). The resin was then washed with DMF (6×1.7 L). The remainder of the compound was synthesized by performing three cycles of acylation with bromoacetic acid and displacement with an amine.

General acylation conditions (0.061 mol resin):

Resin-bound amines were bromoacetylated by in situ, activation with DIC. To the oligomer-resin was added a DMF solution of bromoacetic acid (0.67M, 900 mL) followed by DIC (neat, 93 mL, 0.60 mol). The reaction mixture was agitated for 30 min at room temperature. The mixture was drained and the reaction was repeated once. The resin was washed with DMF (3×1.7 L).

General displacement conditions (0.61 mol):

Resin-bound bromoacetamides were displaced by the addition of the amine as a solution in DMSO (1–2M, 1.0L). The reaction mixture was agitated at room temperature for 2 hours. The reaction mixture was drained and the resin was washed with DMF (3×1.7 L). Phenethylamine and 4-aminobiphenyl were used at .2.0M concentration, while tyramine and phenethylhydrazine were used at 1.0M.

General Cleavage and Purification:

After completion of the synthesis the resin was washed with $CH_2Cl_2$ (3×1.7 L) and air dried for 5 minutes. The full length trimer was cleaved from the resin (00.61 mol) by treatment with 95% TFA/5% water (1.5 L) at room temperature for 15 minutes. The resin was then washed with 95% TFA/5% water (1×1.0 L) and $CH_2Cl_2$ (1×1 L). The filtrates were pooled and the solvent removed by rotary evaporation. The residue was dissolved in glacial acetic acid (150 mL) and lyophilized.

B.) Synthesis of Nhtyr-Nbiph-Nhphe (2279)

The compound Nhtyr-Nbiph-Nhphe was synthesized as described in part A) above, using phenethylamine as the first amine added, 4-aminobiphenyl as the second amine added, and 4-hydroxyphenethylamine as the third amine added.

After completion of the synthesis the resin was washed with $CH_2Cl_2$ (3×1.7 L) and air dried for 5 minutes. The full length trimer was cleaved from the resin (0.061 mol) by treatment with 95% TFA/5% water (1.5 L) at room temperature for 15 minutes. The resin was then washed with 95% TFA/5% water (1×1.0 L) and $CH_2Cl_2$ (1×1 L). The filtrates were pooled and the solvent removed by rotary evaporation. The residue was dissolved in glacial acetic acid (150 mL) and lyophilized to afford a light yellow powder (1.7 g, 82% yield). The purity of the crude product was determined to be 90% by reverse-phase HPLC. The product was characterized by FAB-mass spectrometry ($MH^+ = 565$).

C.) Synthesis of Nhtyr-Npop-Nhphe

The compound Nhtyr-Npop-Nhphe was synthesized as described in part A) above, using phenethylamine as the first amine added, 4-amino-1-phenoxybenzene as the second amine added, and 4-hydroxyphenethylamine as the third amine added.

D.) Synthesis of Backbone Variants

Proceeding as described in part A) above, but substituting 3-bromopropanoic acid and 2-bromopropanoic acid for bromoacetic acid at some positions, the following compounds were prepared:

Nhtyr-Nbiph-Nmhphe;
Nhtyr-Nbiph-Nphphe;
Nphtyr-Nbiph-Nhphe; and
Nhtyr- Npbiph-Nhphe.

E.) Synthesis of Additional Compounds

Proceeding as described in part A) above, but substituting phenethylamine, phenethylhydrazine and 3,4-methylenedioxyphenethylamine for tyramine, the compounds Nhphe-Nbiph-Nhphe, Nzhphe-Nbiph-Nhphe and Noco-Nbiph-Nhphe were prepared. The compound Nhphe-Nbiph-Nhphe was additionally N-benzylated to produce Bz-Nhphe-Nbiph-Nhphe.

Similarly, proceeding as described in part A) above, but substituting 3-trifluoromethylphenethylamine, 2-chlorophenethylamine, 3-chlorophenethylamine, 4-chlorophenethylamine, 2,4-dichlorophenethylamine, 3-bromophenethylamine, 4-iodophenethylamine, 3-hydroxyphenethylamine, 4-hydroxyphenethylamine, 2,4-dihydroxyphenethylamine, 2methylphenethylamine, 3-methylphenethylamine, 4-methylphenethylamine, 2,4-dimethylphenethylamine, 2,4,6-trimethylphenethylamine, 3-ethylphenethylamine, 4-ethylphenethylamine, 4-hexylphenethylamine, 3-nitrophenethylamine, 2-aminophenethylamine, 4-aminophenethylamine, 2,4-diaminophenethylamine, 2-methoxyphenethylamine, 3-methoxyphenethylamine, 4-methoxyphenethylamine, 2,4-dimethoxyphenethylamine, 2,4,6-trimethoxyphenethylamine, 3,4-dimethoxyphenethylamine, 2-ethoxyphenethylamine, 3-ethoxyphenethylamine, 4-ethoxyphenethylamine, 3-propoxyphenethylamine, 4-butoxyphenethylamine, 4-t-butoxyphenethylamine, 3-methoxymethylphenethylamine, 4-methoxymethylphenethylamine, 3-(2-methoxyethyl)phenethylamine, 4-(2-methoxyethyl)phenethylamine, 4-(2hydroxyethyl)phenethylamine, 4-(3-hydroxypropyl)phenethylamine, 4-(2-hydroxyethoxy)phenethylamine, 4-phenylphenethylamine, 4-(2-chlorophenyl)phenethylamine, 4-(2-aminophenyl)phenethylamine, 3-(2,4,6-trimethylphenyl)phenethylamine, 4-phenoxyphenethylamine, 4-(3-chlorophenoxy)phenethylamine, 4-(4-aminophenoxy)phenethylamine, 3-benzylphenethylamine, 4-phenethylphenethylamine, 3-acetylphenethylamine, 4-acetylphenethylamine, 4-(2-phenoxyethyl)phenethylamine, and 3-benzyloxyphenethylamine for phenethylamine, and/or 3'-trifluoromethyl-4-aminophenyl, 2'-chloro-4-aminobiphenyl, 3-chloro-4aminobiphenyl, 4'-chloro-4-aminobiphenyl, 2',4'-dichloro-4aminobiphenyl, 3-bromo-4aminobiphenyl, 4'-iodo-4-aminobiphenyl, 3'-hydroxy-4-aminobiphenyl, 4'-hydroxy-4aminobiphenyl, 2',4'-dihydroxy-4-aminobiphenyl, 2'-methyl-4-aminobiphenyl, 3'-methyl-4aminobiphenyl, 4'-methyl-4-aminobiphenyl, 2',4'-dimethyl-4-aminobiphenyl, 2',4',6'-trimethyl-4'-aminobiphenyl, 2',3,4',5,6'-pentamethyl-4-aminobiphenyl, 3'-ethyl-4-aminobiphenyl, 4'-ethyl-4-aminobiphenyl, 4'-hexyl-4-aminobiphenyl, 340 -nitro-4-aminobiphenyl, 2'-amino-4-aminobiphenyl, 4'-amino-4-aminobiphenyl, 2',4'-diamino-4-aminobiphenyl, 2'-methoxy-4-aminobiphenyl, 3'-methoxy-4-aminobiphenyl, 4'-methoxy-4-aminobiphenyl, 2',4'-dimethoxy-4-aminobiphenyl, 2',4',6'-trimethoxy-4-aminobiphenyl, 3',4'-dimethoxy-4-aminobiphenyl, 2'-ethoxy-4-aminobiphenyl, 3'-ethoxy-4-aminobiphenyl, 4'-ethoxy-4-aminobiphenyl, 3'-propoxy-4-aminobiphenyl, 4'-butoxy-4-aminobiphenyl, 4'-t-butoxy-4amninobiphenyl, 3'-methoxymethyl-4-aminobiphenyl, 4'-methoxymethyl-4-aminobiphenyl, 3'-methoxyethyl-4-aminobiphenyl, 4'-methoxyethyl-4-aminobiphenyl, 4'-hydroxyethyl-4aminobiphenyl, 4'-hydroxypropyl-4-aminobiphenyl, 4'-hydroxyethoxy-4-aminobiphenyl, 4'-phenyl-4-aminobiphenyl, 4'-(2-chlorophenyl)-4-aminobiphenyl, 4'-(2-aminophenyl)-4aminobiphenyl, 3'-(2,4,6-trimethylphenyl)-4-aminobiphenyl, 4'-phenoxy-4-aminobiphenyl, 4'-(3-chlorophenoxy)-4-aminobiphenyl, 4'-(4-aminophenoxy)-4-aminobiphenyl, 3'-benzyl- 4-aminobiphenyl, 4'-phenethyl-4-aminobiphenyl, 3'-acetyl-4-aminobiphenyl, 4'-acetyl-4-aminobiphenyl, 4'-(2-phenoxyethyl)-4-aminobiphenyl, and 3'-benzyloxy-4-aminobiphenyl for 4-aminobiphenyl, and/or phenethylamine, 3-trifluoromethylphenethylamine, 2-chlorophenethylamine, 3-chlorophenethylamine, 4-chlorophenethylamine, 2,6-dichlorophenethylamine, 3-bromophenethylamine, 4-fluorophenethylamine, 3-hydroxyphenethylamine, 2,5-dihydroxyphenethylamine, 2-methylphenethylamine, 3-methylphenethylamine, 4- methylphenethylamine, 2,4-dimethylphenethylamine, 2,4,6-trimethylphenethylamine, 3-ethylphenethylamine, 4-ethylphenethylamine, 4-hexylphenethylamine, 3-nitrophenethylamine, 2-aminophenethylamine, 4-aminophenethylamine, 2,4-diaminophenethylamine, 2-methoxyphenethylamine, 2,5-dimethoxyphenethylamine, 2,3-dimethoxyphenethylamine, 3,5-dimethoxyphenethylamine, 3,4,5-trimethoxyphenethylamine, 3-methoxyphenethylamine, 4-methoxyphenethylamine, 2,4-dimethoxyphenethylamine, 2,4,6-trimethoxyphenethylamine, 3,4dimethoxyphenethylamine, 2-ethoxyphenethylamine, 3-ethoxyphenethylamine, 4-ethoxyphenethylamine, 3-propoxyphenethylamine, 4-butoxyphenethylamine, 4-t-butoxyphenethylamine, 3-methoxymethylphenethylamine, 4-methoxymethylphenethylamine, 3-methoxyethylphenethylamine, 4-methoxyethylphenethylamine, 4-hydroxyethylphenethylamine, 4hydroxypropylphenethylamine, 4-hydroxyethoxyphenethylamine, 4-phenylphenethylamine, 4-(2-chlorophenyl)phenethylamine, 4-(2-aminophenyl)phenethylamine, 3-(2,4,6-trimethylphenyl)phenethylamine, 4-phenoxyphenethylamine, 4-(3-chlorophenoxy)phenethylamine, 3,4-methylenedioxyphenethylamine, 6-methoxy-3,4-methylenedioxyphenethylamine, 2-methoxy-3,4-methylenedioxyphenethylamine, 4,5-methylenedioxyphenethylamine, 3-methoxy-4,5-methylenedioxyphenethylamine, 4-(4-aminophenoxy)-phenethylamine, 3-benzylphenethylamine, 4-phenethylphenethylamine, 3-acetylphenethylamine, 4-acetylphenethylamine, 4-(2-phenoxyethyl)phenethylamine, and 3-benzyloxyphenethylamine for 4hydroxyphenethylamine, the corresponding compounds are prepared.

EXAMPLE 2

Activity

Preparation of Rat Forebrain Membranes:

Rat brains were purchased from Animal Technologies, Tyler, Tex., and shipped on wet ice within 24 hours after being harvested. The forebrains were dissected and homogenized with a Tissue Tearor in 50 mM Tris, pH 7.5, containing 20 mM NaCl, 5 mM EGTA, 2 mM $MgCl_2$, 21 µg/mL aprotinin, 0.5 mg/L leupeptin, 0.7 mg/L pepstatin, 0.2 mM PMSF. Each brain is homogenized in approximately 5 mL of this buffer. The homogenate is then spun at 1000 RPM (75×g) in a Sorval RC-5B centrifuge (SS-34 rotor) for 10 min. The pellets are discarded and the supernatants then respun at 17,000 RPM (22,500×g) for 15 min. The pellets were then resuspended in the same buffer as above containing 5 mM EDTA and no $MgCl_2$ (1 brain/mL). Membranes were stored in 1 mL aliquots at −70° C.

Binding Assay:

Thawed membranes were dispersed into a homogenous solution by passing them through a 22 gauge needle 5 times. To initiate the assay, 50 µL of membrane were dispensed into a plastic 12×75 mm tube containing 1 mL of 50 mM Tris, pH 7.5, 0.5 nM $^3$H-Prazosin (New England Nuclear), and the compounds to be tested. Nonspecific binding was determined as $^3$H-Prazosin bound in the presence of 5 µM unlabeled prazosin. Incubation was for 1 hr at room temperature. Unbound radioactivity was removed by rinsing the membranes on Whatman GF/B glass fiber filters. Each filter was washed 3 times with 3 mL of 50 mM Tris, pH 7.5, 4° C. Filters were soaked overnight in 5 mL of Beckman ReadySafe scintillation cocktail then counted for one minute in a Wallac 1409 liquid scintillation counter.

$IC_{50}$ and $K_i$ values were determined for some of the compounds prepared (Table I):

TABLE I

| Compound | $IC_{50}$ and $K_i$ values | |
|---|---|---|
|  | $K_i$ | $IC_{50}$* |
| Nhtyr—Nbiph—Nhphe | 7 nM | 19 nM |
| Nhtyr—Nbiph—Nbhm | 313 nM | 1.4 µM |
| Nhtyr—Npop—Nhphe | 140 nM | 490 nM |

*$IC_{50}$s determined at a receptor concentration of 10 µM.

Percent inhibition was also determined for the following compounds at 100 nM receptor concentration (Table II):

TABLE II

| Compound | Inhibition at 100 nM |
|---|---|
|  | Percent Inhibition |
| Bz—Nhphe—Nbiph—Nhphe | 24.8% |
| Nzhphe—Nbiph—Nhphe | 53.9% |
| Noco—Nbiph—Nhphe | 23.6% |
| Nhtyr—Nbiph—Nphphe | 48.3% |
| Nphtyr—Nbiph—Nhphe | 22.7% |
| Nhtyr—Npbiph—Nhphe | 20.3% |
| Nhtyr—Nbiph—Nmhphe | 21.2% |

What is claimed:
1. A compound of the formula:

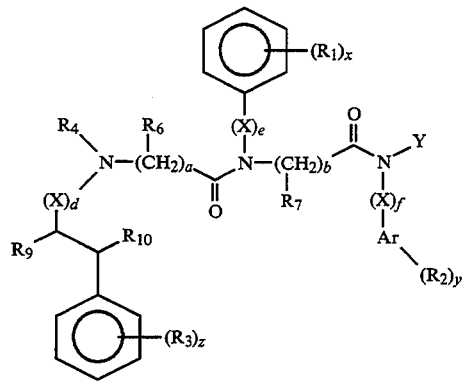

wherein
Ar is phenyl, benzyl, phenethyl, naphthyl, 3,4-methylenedioxyphenyl, or

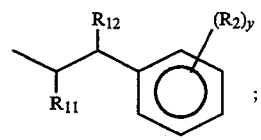

X is —NH— or —$CH_2$—;
Y is H, lower alkyl,-aryl, aryl-lower alkyl, acyl or

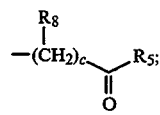

each $R_1$, $R_2$, and $R_3$ is independently H, OH, $NH_2$, $NO_2$, halo, lower alkyl, halo-lower alkyl, lower alkoxy, halo-lower alkoxy, lower alkoxy-lower alkyl, hydroxy-lower alkyl, hydroxy-lower alkoxy, lower alkoxy-carbonyl, aryl, aryloxy, aryl-lower alkyl, aryloxy-lower alkyl, or

where $R_{13}$ is H, OH, $NH_2$, halo, lower alkyl, halo-lower alkyl, lower alkoxy, halo-lower alkoxy, lower alkoxy-carbonyl, aryl, aryloxy, aryl-lower alkyl, or aryloxy-lower alkyl;
$R_4$ is H, lower alkyl, aryl, aryl-lower alkyl, or acyl;
$R_5$ is OH, $NH_2$, OR, or NHR, where R is lower alkyl, aryl, or aryl-lower alkyl;
$R_6$, $R_7$, and $R_8$ are each independently H, lower alkyl, aryl, or aryl-lower alkyl;
$R_9$ and $R_{11}$, are each independently H, lower alkyl, aryl, or aryl-lower alkyl;
$R_{10}$ and $R_{12}$ are each independently H, lower alkyl, aryl, aryl-lower alkyl, halo, or hydroxy;
a, b, and c are each independently 1 or 2;
d, e, and f are each independently 0 or 1;
w, x, y, and z are each independently 0, 1, 2, 3, 4, or 5;
and pharmaceutically acceptable salts, esters, and amides thereof.

2. The compound of claim 1, wherein Y is

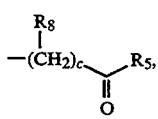

$R_5$ is $CONH_2$, and a, b, and c are each 1.

3. The compound of claim 2, wherein Ar is

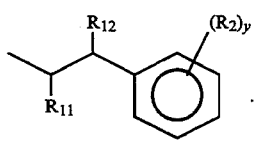

4. The compound of claim 3, wherein z is 1, and $R_3$ is OH in the 4 position.

5. The compound of claim 4, wherein y is 0.

6. The compound of claim 5, wherein $R_4$, $R_9$, $R_{10}$, and $R_{11}$ are each H.

7. The compound of claim 6, wherein x is 1, and $R_1$ is phenyl in the 4 position.

8. The compound of claim 6, wherein x is 1, and $R_1$ is phenoxy in the 4 position.

9. The compound of claim 8, wherein d, e, and f are each 0.

10. The compound of claim 8, wherein e and f are each 0, d is 1, and X is —NH—.

11. The compound of claim 9, wherein $R_2$ is phenyl.

12. A composition for treating a condition susceptible to treatment with an $\alpha_1$-adrenergic receptor agonist or antagonist, which composition comprises:
an effective amount of a compound of Formula 1:

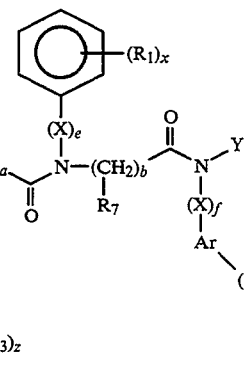

wherein
Ar is phenyl, benzyl, phenethyl, naphthyl, 3,4-methylenedioxyphenyl, or

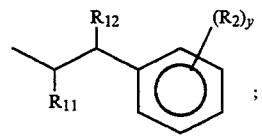

X is —NH— or —$CH_2$—;
Y is H, lower alkyl, aryl, aryl-lower alkyl, acyl or

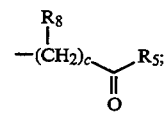

each $R_1$, $R_2$, and $R_3$ is independently H, OH, $NH_2$, $NO_2$, halo, lower alkyl, halo-lower alkyl, lower alkoxy, halo-lower alkoxy, lower alkoxy-lower alkyl, hydroxy-lower alkyl, hydroxy-lower alkoxy, lower alkoxy-carbonyl, aryl, aryloxy, aryl-lower alkyl, aryloxy-lower alkyl, or

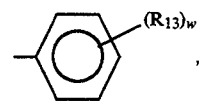

where $R_{13}$ is H, OH, $NH_2$, halo, lower alkyl, halo-lower alkyl, lower alkoxy, halo-lower alkoxy, lower alkoxy-carbonyl, aryl, aryloxy, aryl-lower alkyl, or aryloxy-lower alkyl;
$R_4$ is H, lower alkyl, aryl, aryl-lower alkyl, or acyl;
$R_5$ is OH, $NH_2$, OR, or NHR, where R is lower alkyl, aryl, or aryl-lower alkyl;
$R_6$, $R_7$, and $R_8$ are each independently H, lower alkyl, aryl, or aryl-lower alkyl;
$R_9$ and $R_{11}$, are each independently H, lower alkyl, aryl, or aryl-lower alkyl;
$R_{10}$ and $R_{12}$ are each independently H, lower alkyl, aryl, aryl-lower alkyl, halo, or hydroxy;
a, b, and c are each independently 1 or 2;
d, e, and f are each independently 0 or 1;
w, x, y, and z are each independently 0, 1, 2, 3, 4, or 5;
and pharmaceutically acceptable salts, esters, and amides thereof.

13. A method for treating a hypertension susceptible to treatment with an $\alpha_1$-adrenergic receptor agonist or antagonist, which method comprises:

administering to a subject having hypertension a composition comprising a pharmaceutically acceptable excipient and an effective amount of a compound of Formula 1:

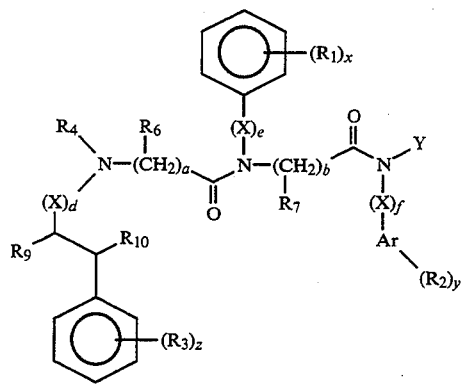

wherein

Ar is phenyl, benzyl, phenethyl, naphthyl, 3,4-methylenedioxyphenyl, or

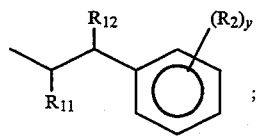

X is —NH— or —CH$_2$—;

Y is H, lower alkyl, aryl, aryl-lower alkyl, acyl or

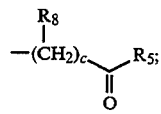

each R$_1$, R$_2$, and R$_3$ is independently H, OH, NH$_2$, NO$_2$, halo, lower alkyl, halo-lower alkyl, lower alkoxy, halo-lower alkoxy, lower alkoxy-lower alkyl, hydroxy-lower alkyl, hydroxy-lower alkoxy, lower alkoxy-carbonyl, aryl, aryloxy, aryl-lower alkyl, aryloxy-lower alkyl, or

where R$_{13}$ is H, OH, NH$_2$, halo, lower alkyl, halo-lower alkyl, lower alkoxy, halo-lower alkoxy, lower alkoxy-carbonyl, aryl, aryloxy, aryl-lower alkyl, or aryloxy-lower alkyl;

R$_4$ is H, lower alkyl, aryl, aryl-lower alkyl, or acyl;

R$_5$ is OH, NH$_2$, OR, or NHR, where R is lower alkyl, aryl, or aryl-lower alkyl;

R$_6$, R$_7$, and R$_8$ are each independently H, lower alkyl, aryl, or aryl-lower alkyl;

R$_9$ and R$_{11}$, are each independently H, lower alkyl, aryl, or aryl-lower alkyl;

R$_{10}$ and R$_{12}$ are each independently H, lower alkyl, aryl, aryl-lower alkyl, halo, or hydroxy;

a, b, and c are each independently 1 or 2;

d, e, and f are each independently 0 or 1;

w, x, y, and z are each independently 0, 1, 2, 3, 4, or 5;

and pharmaceutically acceptable salts, esters, and amides thereof.

* * * * *